United States Patent
Warner et al.

(10) Patent No.: US 11,612,346 B2
(45) Date of Patent: Mar. 28, 2023

(54) QUANTIFICATION AND QUALIFICATION OF ELECTROCARDIOGRAPH RIGHT LEG DRIVE FUNCTION SYSTEM AND METHOD

(71) Applicant: GE Precision Healthcare LLC, Wauwatosa, WI (US)

(72) Inventors: Adrian F. Warner, Wauwatosa, WI (US); Daniel R. Schneidewend, Wauwatosa, WI (US); Rodger F. Schmit, Wauwatosa, WI (US); Timothy P. Stiemke, Wauwatosa, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 588 days.

(21) Appl. No.: 16/740,702

(22) Filed: Jan. 13, 2020

(65) Prior Publication Data

US 2021/0212587 A1    Jul. 15, 2021

(51) Int. Cl.
*A61B 5/25* (2021.01)
*A61B 5/00* (2006.01)
*A61B 5/304* (2021.01)
*A61B 5/332* (2021.01)
(Continued)

(52) U.S. Cl.
CPC .............. *A61B 5/25* (2021.01); *A61B 5/304* (2021.01); *A61B 5/305* (2021.01); *A61B 5/308* (2021.01); *A61B 5/332* (2021.01); *A61B 5/6828* (2013.01); *A61B 5/7221* (2013.01); *A61B 5/7225* (2013.01)

(58) Field of Classification Search
CPC ........... A61B 5/25; A61B 5/304; A61B 5/305; A61B 5/308; A61B 5/332; A61B 5/6828; A61B 5/7221; A61B 5/7225
See application file for complete search history.

(56) References Cited

U.S. PATENT DOCUMENTS

| 5,392,784 | A | 2/1995 | Gudaitis |
| 5,573,011 | A | 11/1996 | Felsing |

(Continued)

OTHER PUBLICATIONS

Freeman et al., "Saturation of the Right-Leg Drive Amplifier in Low-Voltage ECG Monitors", IEEE Transactions on Biomedical Engineering, Jan. 2015, vol. 62, No. 1, pp. 323-330.

(Continued)

*Primary Examiner* — Casey L Kretzer (57) ABSTRACT

In the present invention, a right leg drive RLD monitoring system is employed on a medical computing system/computer, such as an ECG, HEMO and/or EP monitoring, mapping and/or recording system, that includes a number of RLD circuits to be utilized for different procedures or monitoring states to be performed using the system. The RLD monitoring system operates to actively monitor and/or record the feedback voltage to the RLD isolated from the patient. Using the measured feedback voltage data, the RLD monitoring system can identify and determine if the RLD circuit in use is approaching saturation, has reached saturation and the duration the RLD circuit was in saturation. The RLD monitoring system can concurrently and/or subsequently select and/or provide selection information regarding an optimal RLD circuit to be utilized to most effectively perform the desired function of the RLD in the procedure being performed using the monitoring, mapping and/or recording system.

17 Claims, 4 Drawing Sheets

(51) Int. Cl.
　　　*A61B 5/305*　　　(2021.01)
　　　*A61B 5/308*　　　(2021.01)

(56) References Cited

U.S. PATENT DOCUMENTS

| | | | |
|---|---|---|---|
| 2010/0191509 A1* | 7/2010 | Li | A61B 5/30 600/509 |
| 2015/0011901 A1 | 1/2015 | Warner et al. | |
| 2020/0155072 A1* | 5/2020 | Szumanski | A61B 5/6843 |

OTHER PUBLICATIONS

"Driven right leg circuit", https://en.wikipedia.org/wiki/Driven_right_leg_circuit#targetText=A%20Driven%20Right%20Leg%20Circuit,to%20reduce%20Common%2Dmode%20interference.

Venkatesh Acharya, "Improving Common-Mode Rejection Using the Right-Leg Drive Amplifier", Texas Instruments, Application Report, SBAA188, Jul. 2011, 11 pages.

* cited by examiner

RLD SAT. INDEX = X / Y(2) / TIME PERIOD

QUANTIFICATION AND QUALIFICATION OF ELECTROCARDIOGRAPH RIGHT LEG DRIVE FUNCTION SYSTEM AND METHOD

BACKGROUND OF INVENTION

The invention relates generally to electrocardiograph (ECG), hemodynamic (HEMO), electrophysiological (EP) and other types of monitoring, recording or mapping devices or systems that utilize ECG measurements for the monitoring of patients, and particularly to the configuration of the devices and systems for the reduction and/or elimination of noise in the signals to be analyzed.

HEMO/EP devices and systems are used in an increasing number of medical procedures to evaluate various conditions of the patient with which the system is utilized. In many usages of these systems, electrocardiography (ECG) studies record the electrical activity and pathways of a heart to identify, measure and diagnose arrhythmias. In particular, such studies measure electrical changes caused by the depolarization of the heart muscle during each heartbeat. To accomplish this, ECGs utilize electrodes that are combined into channels, the output of which are referred to as a lead.

ECG leads are used in various patient monitoring devices, and also in hemodynamic (HEMO) or electrophysiology (EP) studies, which assess electrical activity through the use of catheters placed in the heart through veins or arteries. More specifically, surface ECG leads attached to the patient are used as the reference for the intra cardiac signals from the catheters. That is, they provide a voltage reference to the patient for measurement by other leads.

In this context, ECG leads may encounter noise from a variety of sources such as wireless electrical devices. Moreover, HEMO/EP studies are typically combined with ablation therapy in which a catheter employs radiofrequency energy, for example, to treat arrhythmias. Various medical devices may also attached to a patient during an HEMO/EP study potentially creating noise. In addition, ECG leads have to measure relatively small electrical signals from the patient, less than 20 $\mu V$ in some instances. As will be appreciated, given the above considerations, achieving acceptable study recordings may be challenging.

To reduce noise, HEMO/EP/ECG systems often utilize a circuit design topology derived from a circuit commonly referred to as "driven right leg" or "right leg drive." Right leg drive (RLD) circuitry is used to eliminate common mode interference noise and to ensure that recording system ground tracks with the patient. In general, RLD circuits introduce a signal into right leg of a patient to cancel common mode noise from the electrodes. There are currently several RLD circuit topologies that are configured and/or tuned for specific study conditions.

However, several common issues can occur with right-leg drive designs. RLD systems generally have only one right-leg drive associated with the ECG/HEMO/EP system and when deployed in challenging scenarios such as the electrophysiology lab, the RDL design is typically tuned to provide all round acceptable performance, but may be less effective in certain specialist scenarios, such as when cardiac ablation is performed.

In addition, monitoring of patients using these types of HEMO/EP/ECG systems is a critical tool in patient care, but its utility is often balanced with frustration from clinicians who are constantly distracted by false alarms. With the right-leg drive (RLD) system that is responsible for reducing ac common-mode noise that couples into the body, even moderate increases in the right-leg skin-electrode resistance can cause the RLD amplifier to saturate. This becomes a significant problem limiting the ability of the RLD to reduce noise, as discussed in Freeman et al., *Saturation of the Right-Leg Drive Amplifier in Low-Voltage ECG Monitors*, IEEE Transactions on Biomedical Engineering, January 2015, Vol. 62, No. 1, pp. 323-330, which is expressly incorporated herein by reference for all purposes. Such saturation can produce ECG noise because the RLD amplifier will no longer be capable of attenuating ac common-mode noise on the body. RLD saturation is particularly a problem for modern ECG monitors that use low-voltage supply levels. For example, for a 12-lead ECG and a 2V power supply, saturation will occur when the right-leg electrode resistance reaches only 2 M$\Omega$.

Accordingly, it is desirable to develop a system for HEMO/EP/ECG systems including very sophisticated RLD patient feedback schemes where the use of a pre-set RLD is no longer used. The system can analyze the variations in performance of the RLD, and in particular RLD saturation, in order to provide indications to the user of the degree of saturation of the RLD in use, and the ability to alter the operation of the RLD to reduce the saturation of the RLD, and thereby provide an optimal configuration for the RLD in use. At the limits of the RLD strategy, the system can also be helpful in indicating to the user that other means of noise reduction may be required, or other strategies employed.

BRIEF DESCRIPTION OF THE INVENTION

There is a need or desire for a system to provide an indication to a user of the degree and duration of saturation of an RLD circuit for a HEMO/EP/ECG system in order to maintain the integrity of the ECG signals being received by the system from the patient. The above-mentioned drawbacks and needs are addressed by the embodiments described herein in the following description.

According to one exemplary aspect of the invention, an RLD monitoring system is employed on a medical computing system/computer, such as an ECG, HEMO and/or EP monitoring, mapping and/or recording system, that includes a number of RLD circuits to be utilized for different procedures or monitoring states to be performed using the monitoring/mapping and/or recording system. The RLD monitoring system operates to actively monitor and/or record the feedback voltage to the RLD isolated from the patient. Using the measured feedback voltage data, the RLD monitoring system can identify and determine if the RLD circuit in use is approaching saturation, has reached saturation and the duration the RLD circuit was in saturation. The RLD monitoring system can concurrently and/or subsequently identify the level of performance of RLD, such as by using a quality index comprised in part of the information regarding the degree and duration of saturation of the RLD, in order to select and/or provide selection information regarding an optimal RLD circuit to be utilized to most effectively perform the desired function of the RLD in the procedure being performed using the monitoring, mapping and/or recording system.

The concept of a continual measurement of the RLD circuit is not a function supported in current ECG/HEMO/EP monitoring and/or recording systems as traditionally there has been only one RLD, and the performance of the RLD has been preselected by the device manufacturer. In a multi-RLD system for a monitoring and/or recording system where there is either a programmable RLD or where a different characteristic for the RLD may be selected, e.g., augmentation of the multi-RLD system with use of a virtual RLD, such as in U.S. Pat. No. 5,392,784, incorporated by reference herein in its entirety for all purposes, either the user or the computer may select or chose a particular performance for the RLD. In these cases either a computer algorithm is required to select the appropriate RLD strategy or the user may manually select from a suitable user interface. In either situation, the user may be able to judge to a degree the noise performance with respect to the recording, but cannot know whether the selected RLD characteristic is approaching saturation, or is in periodic saturation. The method and RLD monitoring system described herein provides both a computer algorithm, and or end user a means of determining the performance of the RLD circuit through reporting by the RLD monitoring system of the degree of saturation, and the period of saturation typically in the form of an index to report these combined effects. This index then provides the user with a ready means to know whether saturation is occurring, and amount of time on a standardized basis this is occurring. This data may also be used as a quality index in the data to highlight the deterioration in the recorded signal.

Based on the information obtained by the RLD monitoring system concerning the degree and duration of saturation of the RLD in use, and the associated index, the RLD monitoring system can automatically select the best setting for the RLD, i.e., how aggressive the RLD filter should be, and provide the user with the index value highlighting the degree of RLD saturation, and the % of time in saturation. This information provides realization of effectiveness of the traditional RLD for noise reduction, and when used in a programmable RLD system, provides feedback on effectivity of the control algorithm under various use conditions for the programmable or multiple RLD system.

According to another aspect of the invention, the RLD monitoring system includes a voltage follower disposed on the RLD in order to isolate a measurement point in the RLD circuit from the patient. The feedback voltage is determined at this measurement point by the RLD monitoring system in order to detect and determine the presence and duration of saturation of the RLD circuit in use.

According to another aspect of the invention, a method of determining and reducing saturation of a right leg drive (RLD) circuit in a data acquisition system including the steps of providing a data acquisition system including a plurality of limb electrodes to be located on the patient, the plurality of electrodes including a right leg electrode, a control unit including a processor configured to receive a plurality of electrophysiological signals from the plurality of limb electrodes and operable to generate an ECG, and at least one right leg drive (RLD) circuit operably connected between a number of the plurality of limb electrodes and the right leg electrode, the at least one RLD circuit including a voltmeter operably connected to the output of the at least one RLD circuit, and supplying input to the RLD circuit, measuring the output from the RDL circuit using the voltmeter to determine an actual output voltage, $V_{ACT}$, comparing $V_{ACT}$ to a saturation voltage $V_{SAT}$ and determining if $V_{ACT}$ exceeds $V_{SAT}$.

According to a further aspect of the invention, a data acquisition system for obtaining electrocardiogram signal (ECG) from a patient includes a plurality of limb electrodes to be located on the patient, the plurality of electrodes including a right leg electrode, a control unit including a processor configured to receive a plurality of electrophysiological signals from the plurality of limb electrodes and operable to generate an ECG and at least one right leg drive (RLD) circuit operably connected between a number of the plurality of limb electrodes and the right leg electrode, the at least one RLD circuit including an RLD amplifier receiving input from the number of the plurality of limb electrodes, a resistor operably connected to the output of the RLD amplifier, a voltmeter operably connected to the output of the resistor, and a voltage follower disposed between the resistor and the right leg electrode.

According to still another aspect of the invention, right leg drive (RLD) circuit for a data acquisition system including a plurality of limb electrodes to be located on the patient, the plurality of electrodes including a right leg electrode, and a control unit including a processor configured to receive a plurality of electrophysiological signals from the plurality of limb electrodes and operable to generate an ECG, includes an RLD amplifier configured to receive input from the number of the plurality of limb electrodes, a resistor operably connected to the output of the RLD amplifier, a voltmeter operably connected to the output of the resistor, and a voltage follower disposed between the resistor and a connection to the right leg electrode.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWING

The drawings illustrate the best mode presently contemplated of carrying out the disclosure. In the drawings

DETAILED DESCRIPTION OF THE DRAWINGS

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Reference will be made below in detail to exemplary embodiments of the invention, examples of which are illustrated in the accompanying drawings. Wherever possible, the same reference characters used throughout the drawings refer to the same or like parts. Although embodiments of the present invention are described as intended for use with electrocardiograph systems, it will be appreciated that embodiments may be adapted for use with other electronic signal monitoring systems that utilize circuit topologies to reduce noise, wander, and/or otherwise increase performance. These may include, but are not limited to, electro encephalogram, electromyogram, electroneurogram, and electromyogram systems.

Moreover, embodiments of the system can be used with various ECG signal acquisition applications such as ECG monitoring in an EP study, stress test ECG, resting ECG, exercise ECG, patient monitoring, defibrillators, etc., involving sensitive electrical signal recording and processing. Sources of noise may include, but are not limited to, the use of ablation equipment, the attachment of multiple medical devices to a subject, ungrounded electrical extension cords, electrical sockets, high-energy consumption equipment, and the like. Embodiments of the inventive system are intended for use in testing subjects, which, as will be appreciated, may be animals or humans.

Electrocardiography (ECG) measures the electrical activity of the heart. It depicts the rate and the regularity of heartbeat as well as the presence of cardiac diseases or damage, arrhythmias etc. The ECG is one of the most important non-invasive diagnostic tools available to cardiologists. An ECG is measured by placing electrodes on the chest and limbs of the patient and measuring the bioelectrical potentials produced by the heart. Electrodes attached to the patient are connected by leads to an ECG monitor or communicate wirelessly to the ECG monitor for further signal processing. The ECG leads can be utilized in connection with hemodynamic (HEMO) or electrophysiology (EP) studies, which assess electrical activity through the use of catheters placed in the heart through veins or arteries. More specifically, surface ECG leads attached to the patient are used as the reference for the intra cardiac signals from the catheters. That is, they provide a voltage reference to the patient for measurement by other leads.

Standard methods for obtaining an ECG from a subject are 3-lead, 5-lead, 12-lead or a 15-lead ECG. 3-lead and 5-lead ECGs are commonly used for routine ECG monitoring at hospitals. The 12-lead ECG monitoring provides much more information e.g. about possible cardiac ischemia, than is obtainable from the 3- or 5-lead ECG. The 3-lead measurement provides six signals: the limb leads I, II, III, aVR, aVL, aVF. This measurement can be done by placing one electrode on each of the patient's four limbs at the wrists and ankles The limb electrodes are referred to as left arm (LA), right arm (RA), left leg (LL), and right leg (RL). However, the invention of the present disclosure is also applicable to a standard 12-lead ECG, where ten electrodes are attached to a patient's body to provide information from the frontal plane from limb leads I, II, III, aVR, aVL and aVF and from the horizontal plane from precordial leads V1, V2, V3, V4, V5 and V6 attached in standard positions on the chest around the heart. With any of these embodiments for the number of leads, as is commonly known in the art, each of the electrodes employed is connected via lead wires and resistor networks to amplifiers to record separate ECG channels or leads from the electrodes.

Figure 1:
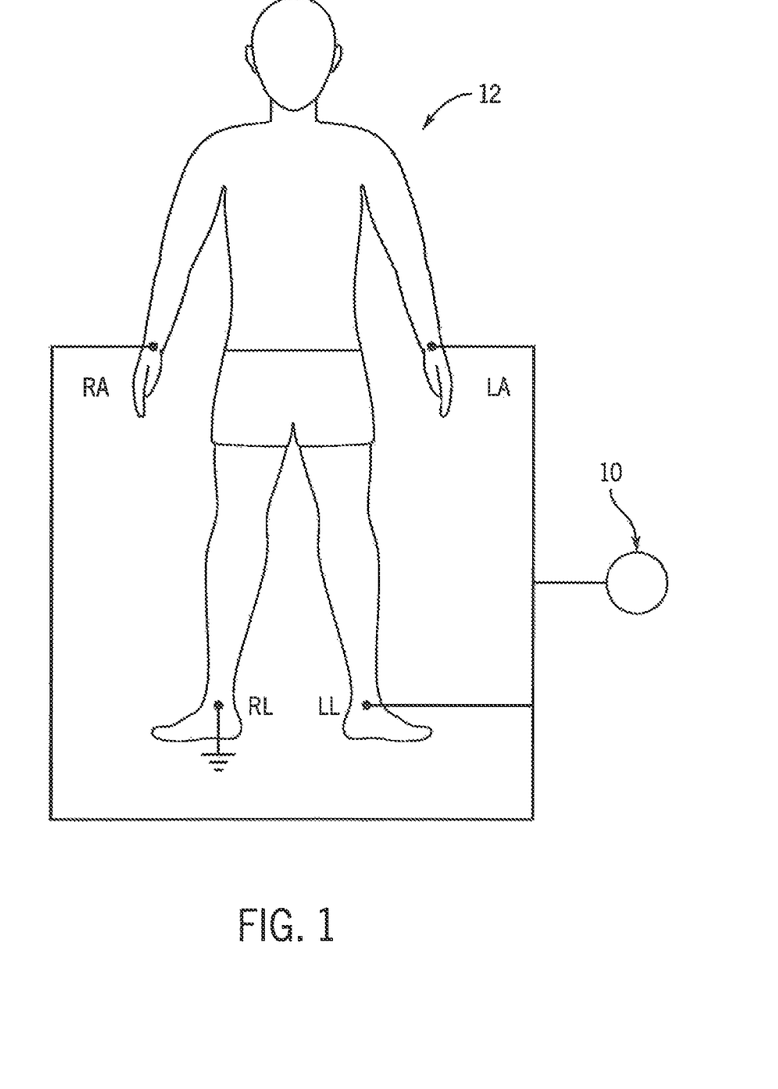
FIG. 1 depicts the standard electrode placement of a 3-lead ECG measurement according to one exemplary embodiment of the present invention.

In the 3-lead system shown in FIG. 1, the frontal leads are obtained with various permutations of the LA, RA, and LL electrodes attached to the patient 12, with the RL electrode serving as an electrical ground. The frontal leads are comprised of the potential between two of the limb electrodes: lead I corresponds to the potential between LA and RA, lead II corresponds to the potential between LL and RA, and lead III corresponds to the potential between LL and LA. Leads aVR, aVL, and aVF, referred to as the augmented leads, are comprised of the potential between one electrode and a reference input, the reference input being the average of two electrodes. For example, lead aVF is the signal between LL and a reference input, where the reference input is the average of the potentials at electrodes RA and LA.

Figure 2:
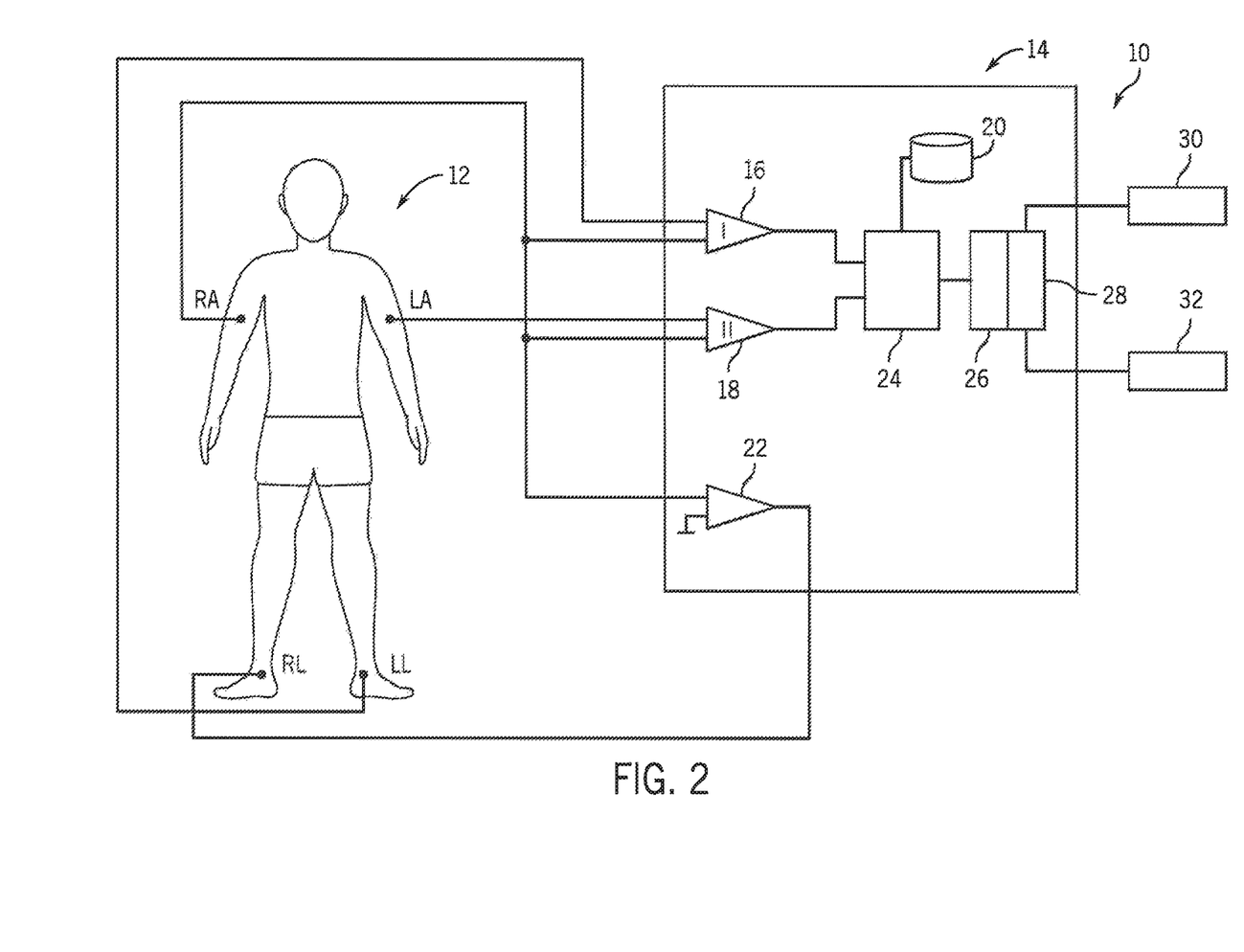
FIG. 2 is a schematic representation of a data acquisition system for the 3-lead ECG measurement according to an exemplary embodiment of the invention.

In FIG. 2 is illustrated a data acquisition system 10 for obtaining electrocardiogram (ECG) signals from a patient 12. The data acquisition system 10 includes a 3-lead ECG measurement unit 14 that measures ECG signals from electrodes RA, LA, LL and RL. As is well known, augmented leads aVR, aVL and aVF are calculated by comparing the measured voltage from each of the limb electrodes to a reference voltage. Amplifiers 16, 18 and 22 are used to compare the signals from the various electrodes to a reference signal from the right arm electrode RA and to feed the output signals from each of the amplifiers to an analog/digital converter 24. Amplifier 22 is a right leg drive (RLD) amplifier that utilizes the RL electrode for equalizing the potential of the human body and the measurement electronics. The A/D converter 24 converts the analog signal into a digital ECG signal that is received by the control unit 26 to be processed by the central processing unit (CPU) 28 within the control unit 26. CPU 28 executes a program of instructions to monitor the level of saturation of the RLD circuit 100 in use and to select an appropriate noise reduction circuit. The control unit 26 may also include, or otherwise be connected to, memory storage 20, such as a solid-state drive. The memory storage 20 contains the program of instructions used to execute embodiments of the inventive method and system. In certain embodiments, the control unit 26 may be external to the system 10 and coupled to the amplifiers 16, 18, 22 via a link, e.g., cable or wireless connection. In certain embodiments, the control unit 26 may be user programmable. Output from the control unit 26/CPU 28 can be presented on a display 30 and interacted with by the user through a user input 32, such as a touchscreen, mouse or keyboard.

Figure 3:
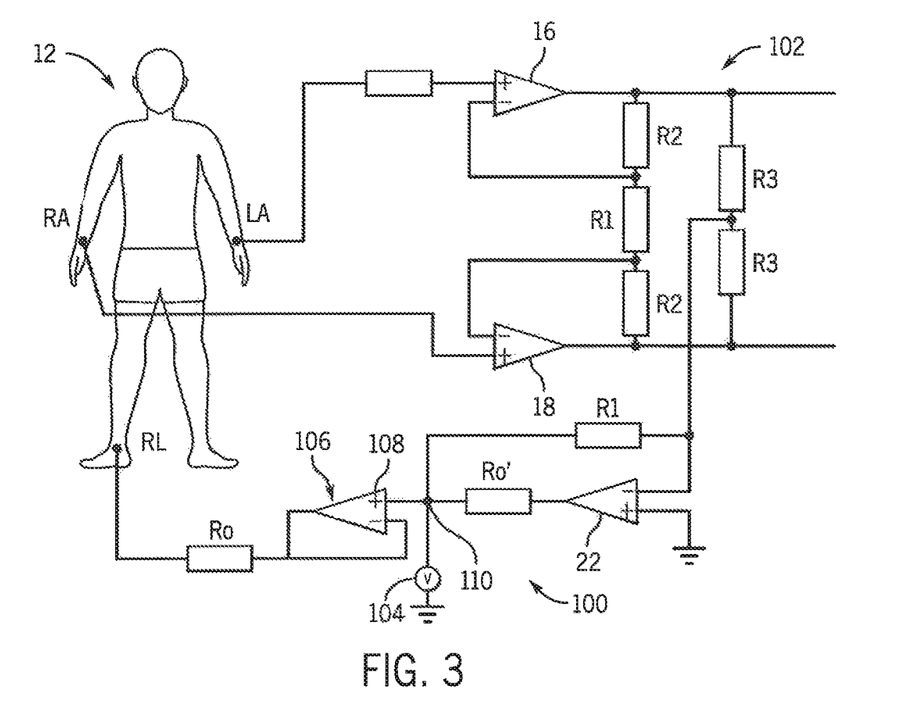
FIG. 3 is a schematic representation of the right leg drive (RLD) circuit according to an exemplary embodiment of the invention employed with the Data acquisition system of FIG. 2.

Referring now to FIG. 3, an exemplary embodiment of the RLD circuit 100 used in the data acquisition system 10 is illustrated. In FIG. 3 the amplifiers 16 and 18 of the measurement unit 14 are illustrated as a portion of a circuit 102 including connections from the amplifiers 16 and 18 to resistors $R_1$, $R_2$ and $R_3$ in order to provide the required signals for leads I, II and III supplied to the converter 24. The RLD circuit 100 is operably connected to the circuit 102 and includes the amplifier 22, a resistor $R_0'$ that receives the output from the amplifier 22 for transmission through a second resistor $R_1$ back to the circuit 102. A voltmeter 104 is connected to the output of the resistor $R_0'$ at point 110, after which the RL signal is directed to a voltage follower 106 including amplifier 108 and a resistor $R_0$ prior to reaching the RL electrode.

Figure 4:
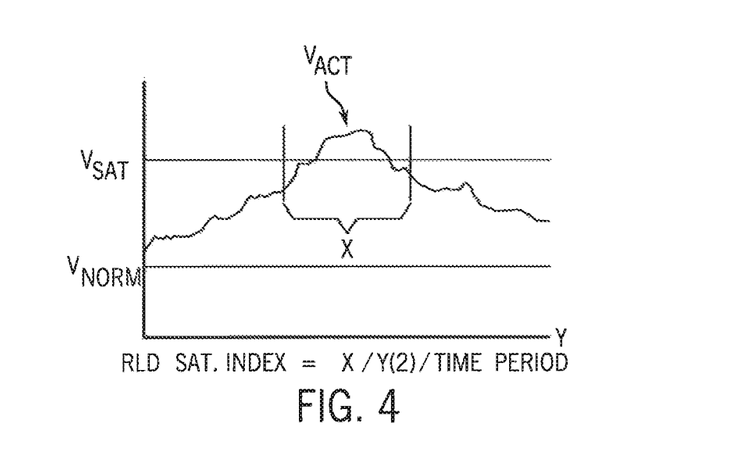
FIG. 4 is a schematic view of an RLD Index measurement performed using the RLD circuit of FIG. 3

As shown in FIG. 4, during operation of the system 10, the control unit 26/CPU 28 monitors the feedback voltage isolated from the patient 12 at point 110 such that the system 10 can record the function of the RLD 100 and the amount of feedback voltage applied to the RLD 100. In this manner the system 10/CPU 26 can identify when: 1) saturation of the RLD circuit 100 is being approached, i.e., the amount the actual output voltage, $V_{ACT}$, of the RLD circuit 100 is over a specified normal voltage output, $V_{NORM}$, or how close $V_{ACT}$ is to a predetermined voltage saturation value $V_{SAT}$, where the output voltage of the RLD circuit 100 exceeds the voltage input to the RLD circuit 100; 2) when saturation has occurred in order to provide an alert to the user, among other actions; and 3) the duration of the saturation of the RLD circuit 100. This measurement can be presented as an RLD index value, with the percentage of saturation of the RLD circuit 100 presented for a uniform time metric, i.e. 1 second, 1 minute, etc. over which the percentage is repeatedly measured and calculated, to provide a ready indication of the level of saturation of the RLD circuit 100. The data from the measurement point 110 can be recorded as a continual data stream along with the patient ECG, or reported periodically through the display 30, or used to provide intelligent warning messages to the user, such as by a warning light or icon (not shown) disposed on the display. It may also be used by a machine learning system (not shown) to train the system 10 on the most optimal settings relative to various conditions encountered by the user.

Figure 5:
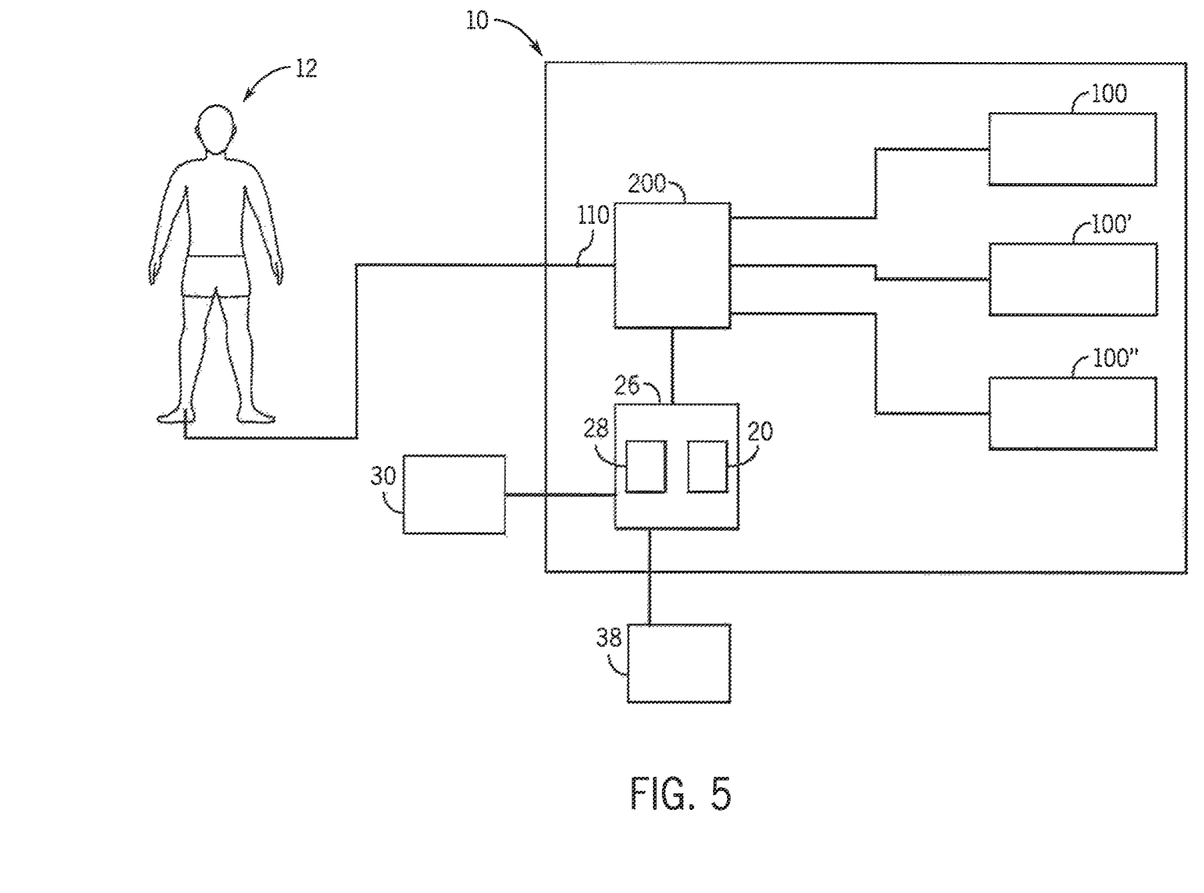
FIG. 5 is a schematic representation of the right leg drive (RLD) circuit according to another exemplary embodiment of the invention employed with the data acquisition system of FIG. 2.

In addition, referring now to FIG. 5, in a data acquisition system 10 such as an ECG or specialist EP/HEMO system featuring multiple RLD circuits 100, 100' and 100" and/or a modifiable or tunable RLD circuit 100 that allows the user to selectively alter the operation of the RLD circuit 100 using a switching circuit 200, such as shown and described in US Patent Application Publication No. US2015/0011901, entitled System And Method For Optimizing Electrocardiography Study Performance, which is expressly incorporated by reference herein in its entirety for all purposes, by providing the RLD saturation index, the system 10 provides both computer algorithm in the CPU 26, and/or the end user a manner of determining the performance of the particular RLD circuit 100, 100' or 100" that is currently in use through reporting by the system 10 of the degree of saturation of the RLD circuit 100, 100' and 100", and the period of saturation of the RLD circuit 100, 100' and 100" in the form of the RLD index to report these combined effects. This RLD index provides the CPU 26/end user with a ready means to know whether saturation is occurring, and amount of time on a standardized basis this is occurring. This data may also be used as a quality index in the data to highlight the deterioration in the recorded signal. Further, using the RLD index, the CPU 26 and algorithm (any examples of what this might ental?—perturbation function, transform function?) can automatically select the best RLD circuit 100, 100' or 100" with its particular associated feedback voltage value for optimal operation of the system 10 based upon how aggressive the RLD circuit 100, 100' or 100" should be in view of the current operating characteristics of the system 10. This information provides realization of effectiveness of the traditional right leg drive, and when used in a programmable right-leg drive system, provide feedback on effectivity of the control algorithm under various use conditions.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A data acquisition system for obtaining electrocardiogram (ECG) signal from a patient, the system comprising:
    a plurality of limb electrodes to be located on the patient, the plurality of electrodes including a right leg electrode;
    a control unit including a processor configured to receive a plurality of electrophysiological signals from the plurality of limb electrodes and operable to generate an ECG signal; and
    at least one saturation monitoring right leg drive (RLD) circuit operably connected between a number of the plurality of limb electrodes and the right leg electrode, the at least one saturation monitoring RLD circuit including:
    an RLD amplifier receiving input from the number of the plurality of limb electrodes;
    a resistor operably connected to the output of the RLD amplifier;
    a voltmeter operably connected to the output of the resistor; and
    a voltage follower disposed between the resistor and the right leg electrode.

2. The data acquisition system of claim 1 wherein the at least one saturation monitoring RLD circuit comprises:
    a plurality of RLD circuits; and
    a switch operable to select an RLD circuit of the plurality of RLD circuits to receive input from the number of the plurality of limb electrodes.

3. The data acquisition system of claim 2 wherein the processor is configured to compare the input to the RLD circuit with the output from the RLD circuit to determine a saturation value for the at least one saturation monitoring RLD circuit.

4. The data acquisition system of claim 3 wherein the processor is configured to determine a saturation index of the at least one RLD circuit.

5. The data acquisition system of claim 4 wherein the saturation index identifies the amount of saturation of the at least one RLD circuit of a specified time period.

6. A saturation monitoring right leg drive (RLD) circuit for a data acquisition system including a plurality of limb electrodes to be located on the patient, the plurality of electrodes including a right leg electrode, and a control unit including a processor configured to receive a plurality of electrophysiological signals from the plurality of limb electrodes and operable to generate an electrocardiogram (ECG) signal, the saturation monitoring RLD circuit comprising:
    an RLD amplifier configured to receive input from the number of the plurality of limb electrodes;
    a resistor operably connected to the output of the RLD amplifier;
    a voltmeter operably connected to the output of the resistor; and
    a voltage follower disposed between the resistor and a connection to the right leg electrode.

7. The saturation monitoring RLD circuit of claim 6 further comprising a second resistor disposed between the voltage follower and the connection to the right leg electrode.

8. The saturation monitoring RLD circuit of claim 6 further comprising:—a plurality of RLD circuits each selectively receiving input from the number of the plurality of limb electrodes; and—a switch configured to selectively connect each of the plurality of RLD circuits with the input from the number of the plurality of limb electrodes.

9. The saturation monitoring RLD circuit of claim 8 wherein the plurality of RLD circuits have different feedback voltage values.

10. The saturation monitoring RLD circuit of claim 6 wherein the RLD circuit is programmable.

11. A method of determining and reducing saturation of a right leg drive (RLD) circuit in a data acquisition system, the method comprising the steps of:
provising a data acquisition system including a plurality of limb electrodes to be located on a patient, the plurality of electrodes including a right leg electrode, a control unit including a processor configured to receive a plurality of electrophysiological signals from the plurality of limb electrodes and operable to generate an electrocardiogram (ECG) signal, and at least one right leg drive (RLD) circuit operably connected between a number of the plurality of limb electrodes and the right leg electrode, the at least one RLD circuit including a voltmeter operably connected to the output of the at least one RLD circuit; and
supplying input to the RLD circuit;
measuring the output from the RDL circuit using the voltmeter to determine an actual output voltage, VACT;
comparing VACT to a saturation voltage VSAT;
determining if VACT exceeds VSAT.

12. The method of claim 11 further comprising the step of providing an alert if VACT exceeds VSAT.

13. The method of claim 11 further comprising the step of determining a duration that VACT exceeds VSAT.

14. The method of claim 13 further comprising the step of providing a saturation index value based on the duration that VACT exceeds VSAT within a set time period.

15. The method of claim 11 further comprising the step of altering the operation of the RLD circuit to reduce saturation of the RLD circuit.

16. The method of claim 11 wherein the RLD circuit includes a plurality of RLD circuits each selectively receiving input from the number of the plurality of limb electrodes; and a switch configured to selectively connect each of the plurality of RLD circuits with the input 5 from the number of the plurality of limb electrodes, and wherein the method further comprises the step of operating the switch to change an RLD circuit in operation to reduce saturation.

17. The method of claim 16 wherein the step of operating the switch is performed automatically by the processor.

* * * * *